United States Patent
Donitzky et al.

(10) Patent No.: US 10,779,989 B2
(45) Date of Patent: Sep. 22, 2020

(54) DEVICE AND METHOD FOR A LASER-ASSISTED EYE-SURGERY TREATMENT SYSTEM

(75) Inventors: Christof Donitzky, Eckental/Eschenau (DE); Christian Wuellner, Moehrendorf (DE); Peter Riedel, Nuremberg (DE)

(73) Assignee: Alcon Inc. (CH)

( * ) Notice: Subject to any disclaimer, the term of this patent is extended or adjusted under 35 U.S.C. 154(b) by 1098 days.

(21) Appl. No.: 14/128,450

(22) PCT Filed: Jul. 4, 2011

(86) PCT No.: PCT/EP2011/003313
§ 371 (c)(1),
(2), (4) Date: Dec. 20, 2013

(87) PCT Pub. No.: WO2013/004255
PCT Pub. Date: Jan. 10, 2013

(65) Prior Publication Data
US 2014/0135747 A1  May 15, 2014

(51) Int. Cl.
*A61F 9/008* (2006.01)
*A61B 34/20* (2016.01)
*A61F 9/009* (2006.01)

(52) U.S. Cl.
CPC .......... *A61F 9/00836* (2013.01); *A61B 34/20* (2016.02); *A61F 9/00827* (2013.01); *A61F 9/009* (2013.01); *A61F 2009/00872* (2013.01)

(58) Field of Classification Search
CPC .. A61F 9/00836; A61F 9/00827; A61F 9/009; A61F 2009/00872; A61B 34/20
See application file for complete search history.

(56) References Cited

U.S. PATENT DOCUMENTS 6,866,661 B2  3/2005  Gray
8,409,177 B1*  4/2013  Lai .......................... A61F 9/008
                                                                    606/4

(Continued)

FOREIGN PATENT DOCUMENTS

CA  2756985 A1  10/2010
CA  2774536 A1  3/2011

(Continued)

*Primary Examiner* — Lynsey C Eiseman
*Assistant Examiner* — Jessandra F Hough
(74) *Attorney, Agent, or Firm* — Kenneth Bassinger, Esq.

(57) ABSTRACT

The invention relates to an apparatus for a laser-assisted eye-surgery treatment system, comprising a first image-acquisition unit that is designed to acquire a first image (39) of an eye to be treated. The apparatus further comprises a computer arrangement which is designed to detect at least one first feature (40') of the eye by means of image processing of the first image, and to determine a position and an orientation of the first feature in a coordinate system (S') of the treatment system. The computer arrangement is also designed to determine a position and an orientation of an incision (66') to be produced in the eye in the coordinate system (S') of the treatment system as a function of the determined position and orientation of the first feature (40') in the coordinate system and as a function of a previously determined relative position and orientation of at least one second feature (64') of the eye with respect to the first feature (40').

13 Claims, 8 Drawing Sheets

(56) References Cited

U.S. PATENT DOCUMENTS

Figure 3:
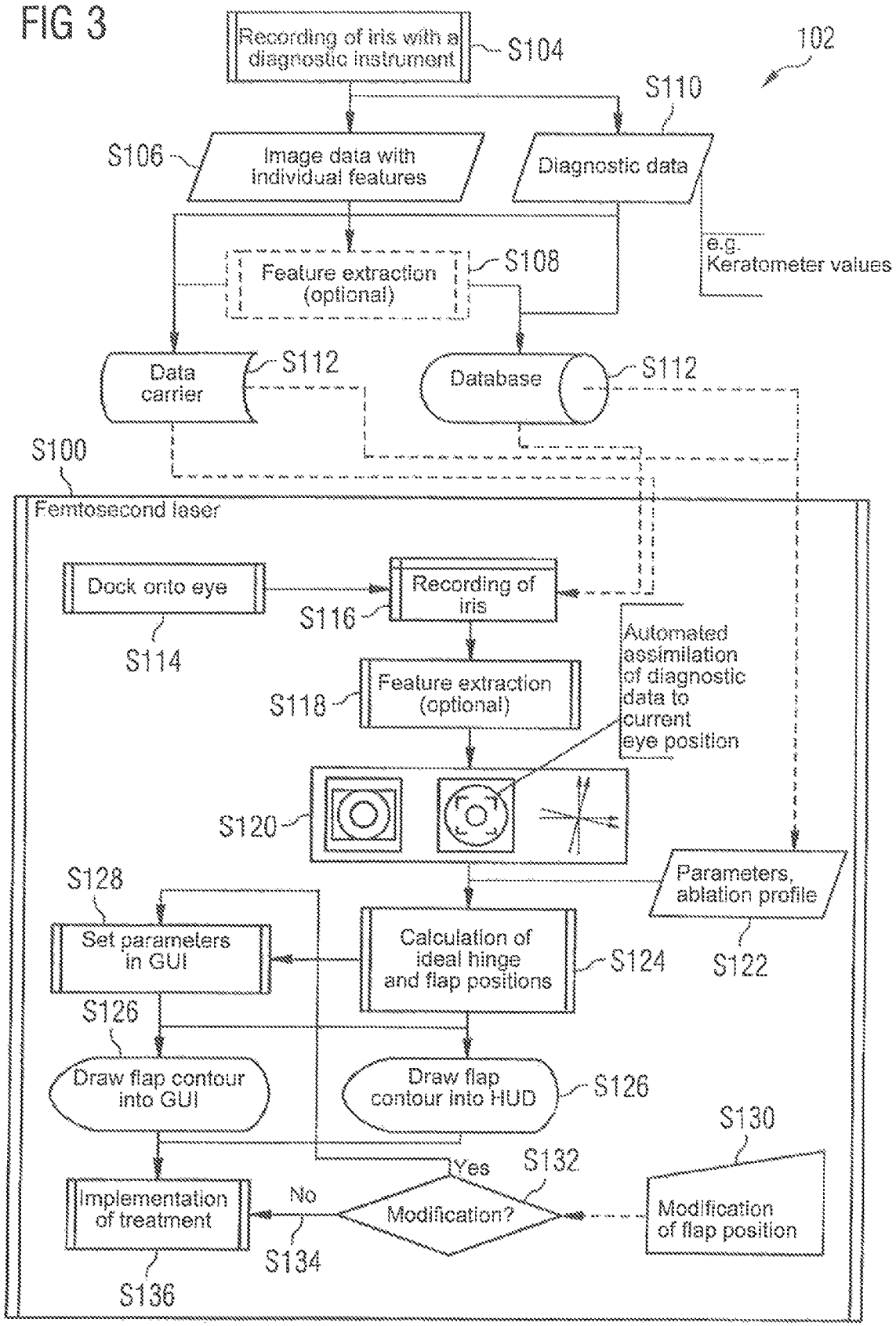

| | | | |
|---|---|---|---|
| 2002/0065511 A1 | 5/2002 | Guimaraes et al. | |
| 2003/0223037 A1 | 12/2003 | Chernyak | |
| 2006/0155265 A1* | 7/2006 | Juhasz | A61F 9/008 606/5 |
| 2008/0051772 A1 | 2/2008 | Suckewer | |
| 2010/0256614 A1 | 10/2010 | Donitzky et al. | |
| 2011/0224657 A1* | 9/2011 | Stevens | A61F 9/008 606/5 |
| 2012/0307207 A1* | 12/2012 | Abraham | A61B 3/113 351/209 |

FOREIGN PATENT DOCUMENTS

| | | |
|---|---|---|
| EP | 1486185 B1 | 9/2006 |
| EP | 1767174 A2 | 3/2007 |
| JP | 2007330801 A | 12/2007 |
| KR | 1020110031214 | 3/2011 |
| RU | 2301650 C1 | 6/2007 |
| WO | 20030049656 A2 | 6/2003 |
| WO | 2006060323 A1 | 6/2006 |
| WO | 2011/035063 A1 | 3/2011 |

\* cited by examiner

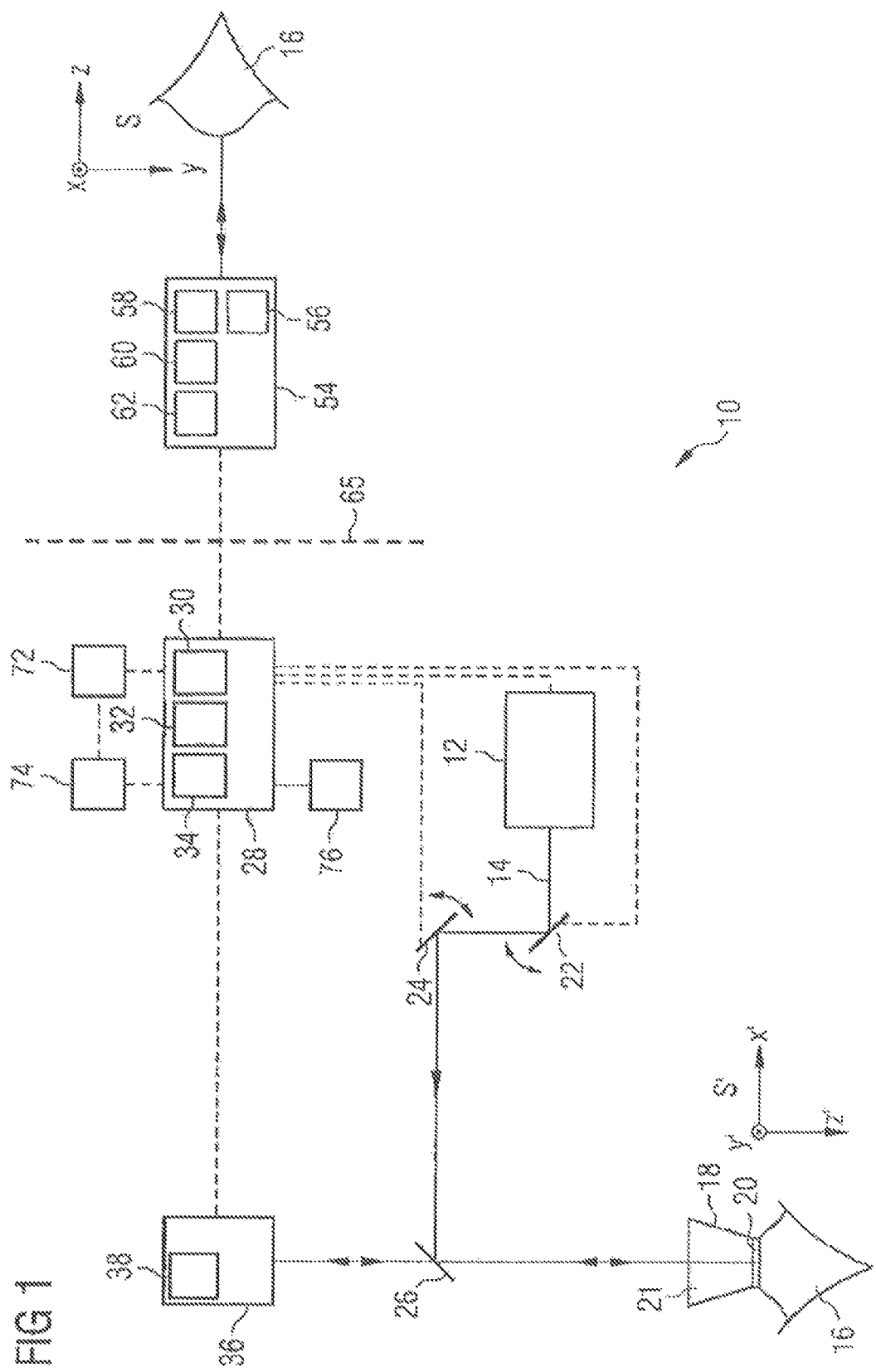

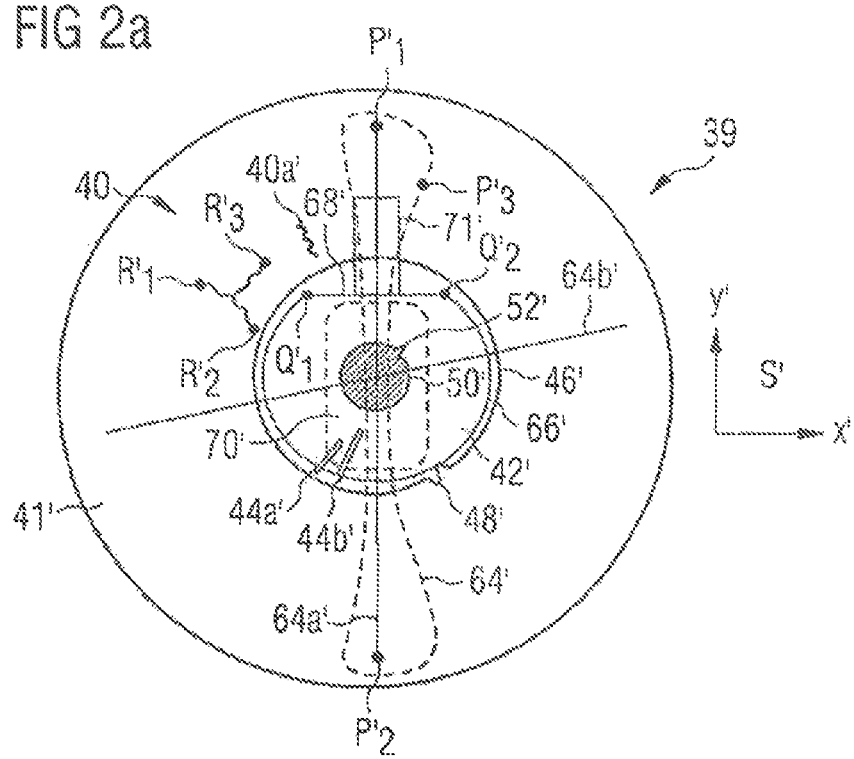
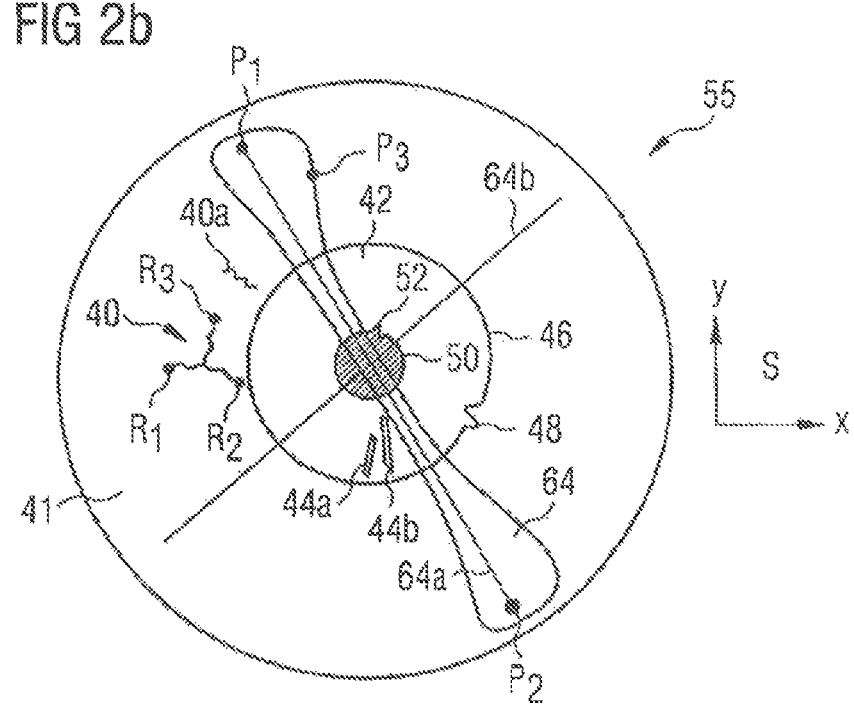

DEVICE AND METHOD FOR A LASER-ASSISTED EYE-SURGERY TREATMENT SYSTEM

CROSS REFERENCE TO RELATED APPLICATIONS

This application is a section 371 national stage phase of International Application No. PCT/EP2011/003313, filed 4 Jul. 2011, titled "APPARATUS AND METHOD FOR A LASER-ASSISTED EYE-SURGERY TREATMENT SYSTEM," which is hereby incorporated by reference in its entirety.

The invention relates to an apparatus and also to a method for use in a laser-assisted eye-surgery treatment system.

In refractive ophthalmological surgery the refractive properties and hence the imaging properties of the eye are changed by operations on the eye of a patient, in order to mitigate or to correct visual defects. One known form of operation is, for example, LASIK (laser in-situ keratomileusis). In this case, a flat corneal incision is made, by which a small disc serving as a cover (customarily designated in specialist circles, even in German, by the English term "flap") is produced which at one point remains firmly connected to the cornea and forms there a hinge (customarily designated by the English term, even in German). Along this hinge the flap can be folded open. As a result, the corneal tissue situated underneath the flap can be exposed, in which by means of suitable laser radiation—customarily radiation of an excimer laser—an ablation of tissue can then be performed in accordance with an erosion profile determined in a manner depending on the visual defect. Subsequently the flap is folded back. Since the epithelium remains largely intact, the healing process is relatively short and painless.

In classical LASIK the flap is cut by a mechanical microkeratome. However, it is also known to cut the flap by means of suitable laser radiation. This variant is customarily known in specialist circles by the term femto LASIK or fs LASIK, because hitherto in such circles pulsed laser radiation with pulse durations within the femtosecond range has customarily been employed. It should of course be pointed out that incisions of tissue can be placed in the human cornea also with shorter or longer pulse durations, for instance within the attosecond or picosecond range. Therefore the term laser-assisted LASIK will be used in the following when it is a question of a form of LASIK in which the flap incision is produced by laser technology.

The invention disclosed herein can in principle be employed in the course of different forms of treatment in which laser radiation is to be positioned in defined manner with respect to the eye. These forms include not only laser-assisted LASIK but also, for example, laser-assisted keratoplasty (lamellar or perforating), laser-assisted corneal lenticule extraction, and other forms of surgery that require the placement of intracorneal incisions.

Laser systems with which incisions in the human eye can be produced typically have a so-called applicator which includes a contact element that is transparent to the laser radiation being used and that provides a contact surface for planar abutment of the eye to be treated. Such applicators are often also designated as the patient interface, because they offer an interface (a mechanical interface) of the laser system to the eye. The applicator may, in turn, have been releasably coupled with, for example, a focusing objective of the laser system. By the applicator being brought into engagement with the eye in such a way that the surface of the eye conforms to the contact surface, the eye can be referenced in relation to the coordinate system of the component of the laser system that is responsible for the spatial control of the focus of the radiation. In this way, a precise production of an incision at the desired point in the eye is possible.

Prior to the implementation of a laser treatment serving for the production of an incision (or, expressed more generally, an incision figure) in the eye, the general problem is that the patient, with his/her eye to be treated, has to be aligned in relation to the laser system. The incision figure is, as a rule, to be produced at a certain position in the eye and also—to the extent that it is not a question of a rotationally symmetrical figure—in a certain orientation to the eye. For a flap incision within the scope of a LASIK treatment, for example, the stipulation applies that said incision is to be produced at the place in the eye where tissue is later to be ablated, i.e. the flap has to cover the zone to be ablated. At the same time, a flap incision possesses an asymmetry in the form of the hinge. Above all, if the zone to be ablated is likewise rotationally asymmetrical, for example because an astigmatism is to be rectified, it is readily comprehensible that the flap hinge should be situated in a certain optimal location in relation to the designated ablation zone, in order, with the smallest possible flap size, nevertheless to be able to carry out the ablation in unhindered manner in all designated regions. In the case of astigmatism, for example, it may be desirable and necessary to align the flap hinge in defined manner in relation to the astigmatic part of the corneal surface, that is to say, in relation to the axis of the astigmatism.

The requisite alignment of the eye of the patient in relation to the laser system may therefore relate not only to the position but also to the orientation of the eye relative to the laser system. 'Orientation' here means, quite generally, the alignment of a first axis, which characterises a direction of extension of a first extensive object, in relation to a second axis, which characterises a direction of extension of a second extensive object, or in relation to a given coordinate system.

Hitherto it has, as a rule, been customary that this alignment of the patient in relation to the laser system has been carried out by the treating physician manually and by eye, where appropriate with the aid of a microscope. In this connection he/she customarily attempts to arrange the applicator as centrally as possible with respect to certain contours of the eye, and to align it in its orientation with respect to certain contours of the eye. This can be done, for example, by appropriate alignment of a patient couch on which the patient is lying, or/and by appropriate manoeuvring of a beam arm, bearing the applicator, of the laser system. Because the applicator, in turn, is capable of being attached to the laser system only in a certain orientation, this orientation alignment of the applicator in relation to the eye signifies at the same time an orientation alignment of the laser system as a whole in relation to the eye.

A disadvantageous aspect of this procedure is that the quality of the alignment depends on the experience and skill of the physician, and hence may be more or less subject to considerable fluctuations. In addition, the manual alignment by the physician requires a comparatively long time. However, the aim generally is to keep the overall operating time as short as possible, in order to keep the inconvenience for the patient as slight as possible. The longer the process of docking the eye onto the applicator lasts, because in this phase the physician has to laboriously adjust and monitor the correct alignment of the applicator in relation to the eye, the longer the operation lasts overall.

An object of embodiments of the invention is to shorten the process of docking an applicator of the laser system onto the eye in the case of a laser system that is suitable for the laser-assisted placement of intraocular incisions.

In accordance with the invention, an apparatus and a method having the features of the independent claims 1 and 16 have been provided.

The apparatus has been provided for use in a laser-assisted eye-surgery treatment system and includes a first image-acquisition unit configured to acquire a first image of an eye to be treated. Furthermore, the apparatus includes a computer arrangement configured to perform the following steps:

(i) detecting, by image processing of the first image, at least one first feature of the eye, and determining a position and an orientation of the first feature in a coordinate system of the treatment system, (ii) determining a position and an orientation of an incision figure to be produced in the eye in the coordinate system of the treatment system in a manner depending on the determined position and orientation of the first feature in the coordinate system and also in a manner depending on a previously determined relative position and orientation of at least one second feature of the eye in relation to the first feature.

The first feature may relate, for example, to an eye structure that is detectable by image acquisition, such as, for instance, the iris, the pupil, the pupillary centre, the limbus, a scleral blood-vessel arrangement and/or a corneal thickness distribution. The second feature may relate, for example, to an astigmatically deformed corneal region that is capable of being represented by an astigmatism axis. The second feature may, if desired, depend on properties of the first feature. For example, it is conceivable to determine from a corneal thickness distribution an astigmatically deformed corneal region. These are, of course, only examples which on no account are to be understood as being limiting. Other detectable eye features are also conceivable as first or second feature. In particular, stratified features of the eye acquired by means of optical coherence tomography (OCT) are conceivable.

In the case of a LASIK operation, for example an image of the iris of the eye to be treated can be acquired preoperatively at a diagnostic station, and from the image of the iris a suitable eye structure (e.g. a certain scleral blood vessel or a corneal thickness distribution) can be detected as first feature. At the same time, at the diagnostic station the topography of the anterior surface of the cornea can be examined with a keratometer, and keratometer values can be determined that represent the axial location and severity of a corneal astigmatism. Additionally or alternatively, at the diagnostic station a pachymetric recording of the eye can be made by means of optical coherence tomography (OCT) or by means of a Scheimpflug measurement, from which the corneal thickness distribution is determined. The astigmatic zone of the cornea may serve as second feature. To the extent that the recording of the iris, the keratometry and the pachymetry are performed at the same diagnostic station, it can be assumed that the image of the iris is situated in a known relation to the axial location of the astigmatism, determined in the course of the keratometry and/or pachymetry. Therefore reference information can be determined that represents the relative position and the relative orientation of the astigmatism zone in relation to the first feature, for example in vectorial form.

For the actual LASIK operation the patient can be relocated from the diagnostic station to a treatment station which is located, for example, in a different room of the medical practice. The LASIK operation in this exemplary case is to have the objective of correcting a weakness of vision of the eye caused by the astigmatism measured above. This means that the flap has to be cut in such a way that it covers the astigmatism zone, so that, after the flap has been folded back, the astigmatism zone can be treated in ablating manner by means of laser radiation. In this connection, what is important, in particular, is a suitable relative location of the flap hinge with respect to the astigmatism zone. It should, in particular, be ensured that the flap hinge is situated outside the region that would have to be ablated in order to correct the visual defect. That is to say, the flap has to be adapted to the location of the astigmatism zone with regard to its position and orientation (where appropriate, also with regard to its size).

In the case of a flap, it may be desirable that the incision figure defines an auxiliary channel connected to an incision surface of the flap, which is formed by a corresponding auxiliary incision as part of the incision figure. Such an auxiliary channel, which is preferentially connected to said incision surface of the flap in the region of the flap hinge, may serve for the removal of gases that arise in the course of the photodisruptive production of an incision in the eye tissue. The auxiliary channel extends away from the flap and may, for example, extend at least into the region of the limbus of the eye being treated. At its end that is remote from the flap it may emerge on the surface of the eye, or it may terminate deep within the eye tissue. For example, it may extend beneath the conjunctiva of the eye or may extend into the sclera of the eye.

In order to ensure that the auxiliary channel always satisfies the requirement to extend at least into the region of the limbus, in an advantageous further development of the invention there is provision that the computer arrangement is configured to generate, in a manner depending on the determined position and orientation of at least those parts of the incision figure which define the flap, control data for the production of the auxiliary channel in such a manner that the auxiliary channel extends at least into the region of the limbus of the eye and preferentially even beyond the limbus. This makes it possible to generate the necessary control data for the control of the laser radiation always in conformity with the determined position and orientation of the flap, more precisely the determined position and orientation of those elements of the incision figure which define the flap. This may require, in particular, a suitable adaptation of the length of the auxiliary channel, so that the latter extends reliably as far as the limbus or beyond it.

The auxiliary channel may, for example, be formed by a substantially flat incision. Over its length it may have substantially constant width, but it may also vary with regard to its width; for example. it may become progressively wider or alternatively progressively narrower starting from the flap in the direction towards its other end.

Expediently, the auxiliary channel is produced before the flap-defining elements of the incision figure are cut.

As an alternative to a LASIK flap, the incision figure may define a corneal lenticule to be extracted. By extraction of a suitably shaped piece of tissue from the interior of the cornea, likewise a refractive correction of cases of defective vision of the eye can be achieved. Because this piece of tissue is typically approximately lenticular, it is also designated as a lenticule. Since the geometry of the lenticule is dependent upon the defective vision of the eye that is to be rectified, and this is often not exactly rotationally symmetrical but, for example, involves an astigmatism, corneal lenticule extraction is also suitable for application of the invention, by the incision figure defining the lenticule being aligned with regard to position and orientation, where appropriate also with regard to shape or/and size, with respect to a suitable second feature, for instance an astigmatically deformed corneal region. Alternatively or additionally, the position, orientation and/or size of the incision figure of the lenticule can be aligned with respect to the location—acquired by imaging technology—of the pupillary centre of the eye and/or of the corneal thickness distribution of the eye.

At the treatment station the eye of the patient that is to be treated can be brought into contact with an applicator of the laser system so that the eye has been fixed in relation to the applicator. By means of a camera of the laser system, an image of the eye can then be acquired, in which connection a computer of the laser system can evaluate this image by means of suitable image-processing software and can detect therein the first feature, for instance a certain blood vessel or a corneal thickness distribution. As soon as the first feature has been detected, the computer can determine the position and orientation of this feature in a coordinate system of the laser system. On the basis of the aforementioned reference information the computer can then determine the position and orientation of the second feature in the coordinate system of the laser system. Based on the knowledge, acquired in this way, of the position and orientation of the second feature (astigmatism zone) in the coordinate system of the laser system, the computer can thereupon determine a suitable incision figure for the flap and, where appropriate, for the auxiliary channel. In particular, the computer can suitably define the position and orientation of the flap hinge in the coordinate system of the laser system, and it can also determine a suitable shape or/and size of the flap.

Because with this procedure no manual aligning of the eye of the patient in relation to the laser system by the operating surgeon is required, but instead of this the position and orientation of the incision figure can be adapted automatically in computer-assisted manner, the phase from the docking of the applicator onto the eye until the actual start of the process of cutting the incision figure can be kept short. This reduces the inconvenience associated with the operation for the patient.

As already mentioned, the invention may find application, for example, in the course of LASIK operations. For this purpose the incision figure may define a corneal flap with a flap hinge and, where appropriate, with an auxiliary channel serving as gas-venting channel.

In a preferred configuration of the invention the computer arrangement may be configured to determine the position and orientation of a figure element of the incision figure defining the flap hinge in a manner depending on the position and orientation of the first feature in the coordinate system of the treatment system and also in a manner depending on the relative position and orientation of the second feature in relation to the first feature.

To the extent that the at least one second feature includes an astigmatically curved corneal region, the computer arrangement may be configured to determine the position and orientation of the incision figure by taking into account a predetermined set location condition between the flap and the astigmatically curved corneal region.

For example, a hinge axis may have been assigned to the flap hinge, and an astigmatism axis may have been assigned to the astigmatically curved corneal region. The computer arrangement may then be configured to determine the position and orientation of the incision figure by taking into account a predetermined set location condition between the hinge axis and the astigmatism axis. This set location condition between the hinge axis and the astigmatism axis may, for example, predetermine a substantially mutually perpendicular location of the two axes.

The apparatus according to the invention may include a diagnostic instrument with a second image-acquisition unit for acquiring a second image of the eye to be treated. This diagnostic instrument may be configured to detect in the second image, by image processing, the at least one feature, and to generate feature information relating to a position and orientation of each of the two features. Data with regard to position and orientation of the second feature can be obtained by the diagnostic instrument, for example on the basis of topographical measurements of the anterior surface and/or posterior surface of the cornea by means of a keratometer, or on the basis of a measurement of the corneal thickness distribution by means of optical coherence tomography (OCT) or by means of a Scheimpflug camera.

The computer arrangement or even the diagnostic instrument itself may be configured to determine, on the basis of the feature information, the relative position and orientation of the second feature in relation to the first feature.

It is conceivable that the diagnostic instrument and the first image-acquisition unit have been assigned to various workstations in a medical practice.

A database may have been assigned to the diagnostic instrument, in order to store therein the feature information or/and information derived therefrom, with assignment to patient-identifying information. The computer arrangement may in this case have access to the database so that it can determine the relative position and orientation of the second feature in relation to the first feature on the basis of the feature information. It is equally conceivable that the diagnostic instrument itself is configured to determine the relative position and orientation of the second feature in relation to the first feature on the basis of the feature information. In this case a configuration may have been provided in which the diagnostic instrument stores corresponding information about the relative position and orientation of the second feature in relation to the first feature in a database which the computer arrangement can access.

According to a preferred further development, the computer arrangement may be configured to bring about a pictorial representation of the incision figure that illustrates the determined position and orientation of the incision figure in relation to the first feature or/and the second feature or/and a corneal region to be ablated. The pictorial representation enables an operating surgeon to check, prior to the start of the operation and on the basis of his/her own view, whether the position and orientation of the incision figure proposed by the computer arrangement are suitable in the concrete case. For example, the computer arrangement may be configured to bring about the pictorial representation on a monitor or/and by insertion into an observation beam path of an operating microscope.

It cannot be ruled out that the operating surgeon is not in agreement with the suggestion for the position and orientation of the incision figure, and would like to undertake modifications. For this purpose the computer arrangement may be configured to modify the determined position or/and orientation of the incision figure in accordance with a user input, and to modify the pictorial representation of the incision figure in accordance with the modified position or/and orientation.

It is advantageous if the computer arrangement is configured to receive a confirmation, entered by the user, of the position and the orientation of the incision figure, and to generate, in a manner depending on the reception of this confirmation, control data for a laser device, and to control the laser device in accordance with these control data for the purpose of producing the incision figure in the eye.

The first feature or/and the second feature may, in any case as far as the determination of their position and orientation is concerned, for example be represented in each instance by several (for example, two or three) points which may also be designated as pixels or vectors. Both features are preferentially non-punctiform, recognisable objects/structures that span a line segment or an area in an image generated by camera technology, topographically or otherwise and, for example, have a preferred dimension. Each pixel of such an image may, for example, have been defined by two or three coordinate values and/or by at least one grey value or by a colour value.

The feature information may, for example for the first and the second feature, in each instance include a data set that describes a plurality of (for example, three) characteristic points of the first and the second feature in an arbitrary coordinate system. The points of the first feature may in this connection have been represented by three vectors, in which case two relative vectors between a first and a second of these characteristic points and also between the first and a third of the characteristic points may represent two linearly independent coordinate vectors which span an eye-internal coordinate system of the eye and may serve as representatives thereof. Each characteristic point of the second feature can be defined uniquely by the position of the first characteristic point of the first feature and by a linear combination of the two aforementioned coordinate vectors within the eye-internal coordinate system. This makes it possible to reference the positions of the characteristic points of the second feature with respect to the eye-internal coordinate system of the eye that is defined by the first feature. Consequently it is possible to define uniquely a relative position and also a relative orientation of the second feature in relation to the first feature.

At the treatment station it is sufficient if only the first feature is detected in the image acquired by the first image-acquisition unit and the position and orientation thereof in a given coordinate system of the treatment system are determined. Previously obtained information about the relative position and orientation of the second feature in relation to the first feature then permits the computer arrangement to determine the position and orientation of the second feature in the coordinate system of the treatment system unambiguously, without thereby having to detect the second feature itself. The feature information accordingly permits the position and orientation of the second feature in the coordinate system of the treatment system to be determined purely by computation, without a special image acquisition (for instance with a camera or with a topography-measuring instrument) for the second feature having to be carried out at the treatment station. This results in a gain in time in the course of the surgical treatment, since the detection of the second feature can take place within the scope of a preliminary examination at a diagnostic station, but in the course of the treatment itself such a detection is not required.

Advantageously the position and orientation (if desired, also the geometrical shape or/and the size) of the incision figure are suitably determined by the computer arrangement in a manner depending on the determined position and orientation of the second feature in the coordinate system of the treatment system, in order to enable, by using the incision figure, a treatment that successfully corrects a weakness of vision associated with the second feature in a direct manner (e.g. in the case of an intracorneal lenticule extraction or a keratoplasty) or an indirect manner (for instance in the case of a laser-assisted LASIK treatment).

The computer arrangement may be configured to determine the position and orientation (where appropriate, also the shape or/and size) of the incision figure in such a manner that in the case of a flap production a shortest spacing of the hinge axis of the flap hinge from a centre of the eye has a predetermined value, different from zero. The shortest spacing or the predetermined value thereof may have been adapted to the geometrical shape of an ablation zone in which a corneal ablation of eye tissue is to be carried out. The centre of the eye may have been defined, for example, by the pupillary centre or by another structure of the eye, or may have been referenced with respect to such a structure and may be determined by the computer arrangement from the first image acquired by the first image-acquisition unit.

The diagnostic instrument may have been equipped with a camera system for acquiring the second image and also with a topography-measuring device which permits the topography of the cornea to be determined and, on the basis of the topographic data determined in this way, permits the position and orientation of a certain corneal region, for instance an astigmatically deformed corneal region, to be determined. The position and orientation of this corneal region (second feature) can in this case advantageously be referenced with respect to an eye-internal coordinate system that has been defined by the first feature of the eye. This first feature can be detected on the basis of the images of the camera system, and can be acquired in terms of position and orientation.

The pictorial representation of the incision figure according to its determined position and orientation (and, where appropriate, its determined shape and size) may, for example, illustrate the outline contour of a flap (i.e. flap hinge and flap edge). In particular, it may be advantageous if the pictorial representation illustrates not only the incision figure, or at any rate relevant parts of the incision figure, but also the second feature. Such an illustration of the second feature can be brought about, for example in the case of an astigmatically deformed corneal region, by a line-like representation of the outline contour of the astigmatic region or/and by a representation of an astigmatism axis. For the operating surgeon this enables a particularly simple check as to whether the incision figure determined by the computer arrangement is suitable in view of the location of the astigmatic corneal region (or generally: in view of the location of the second feature). The pictorial representation may, for example, be inserted into an image of the eye, in which case this image may be one that is recorded by a camera at the treatment station, or it may be one that the operating surgeon sees through an operating microscope. In the former case, a visualisation of the pictorial representation on a monitor is expedient; in the latter case, the pictorial representation can be inserted by a suitable insertion device (in the manner of a head-up display, HUD) into the observation beam path of the operating microscope.

An input device may have been provided, via which the operating surgeon or an assistant can modify, by manual input, the incision figure previously determined by the computer arrangement. Expediently such a modification of the incision figure is reflected in the pictorial representation of the same, i.e. the pictorial representation is adapted as soon as the user undertakes modifications to the incision figure via the input device. The position and orientation of the incision figure determined by the computer arrangement can accordingly be interpreted by the operating surgeon as a suggestion which he/she can modify as he/she desires. An enabling of the laser system for producing the incision figure may in this case require a confirmation input on the part of the operating surgeon, regardless of whether the operating surgeon would like to accept the suggestion of the computer arrangement immediately, or whether he/she would previously like to make modifications. The modifications that are capable of being undertaken by the operating surgeon may not only relate to the position and orientation of the incision figure; above and beyond this, it may be conceivable that the operating surgeon can also modify the geometrical shape or/and the size of the incision figure individually via the input device.

In the foregoing an astigmatically deformed corneal region was specified as an example of a second feature in the sense of the invention. It will be understood that other structures or regions of the eye may serve as second feature, for instance a cataract in the human lens if the invention is to be employed within the scope of a cataract operation in which the incision figure is to include an incision in the human lens and/or in the capsular bag, which for instance serves as access to the lens. In this respect the invention is by no means limited to corneal incision figures, and also not to corneal features.

Figure 4:
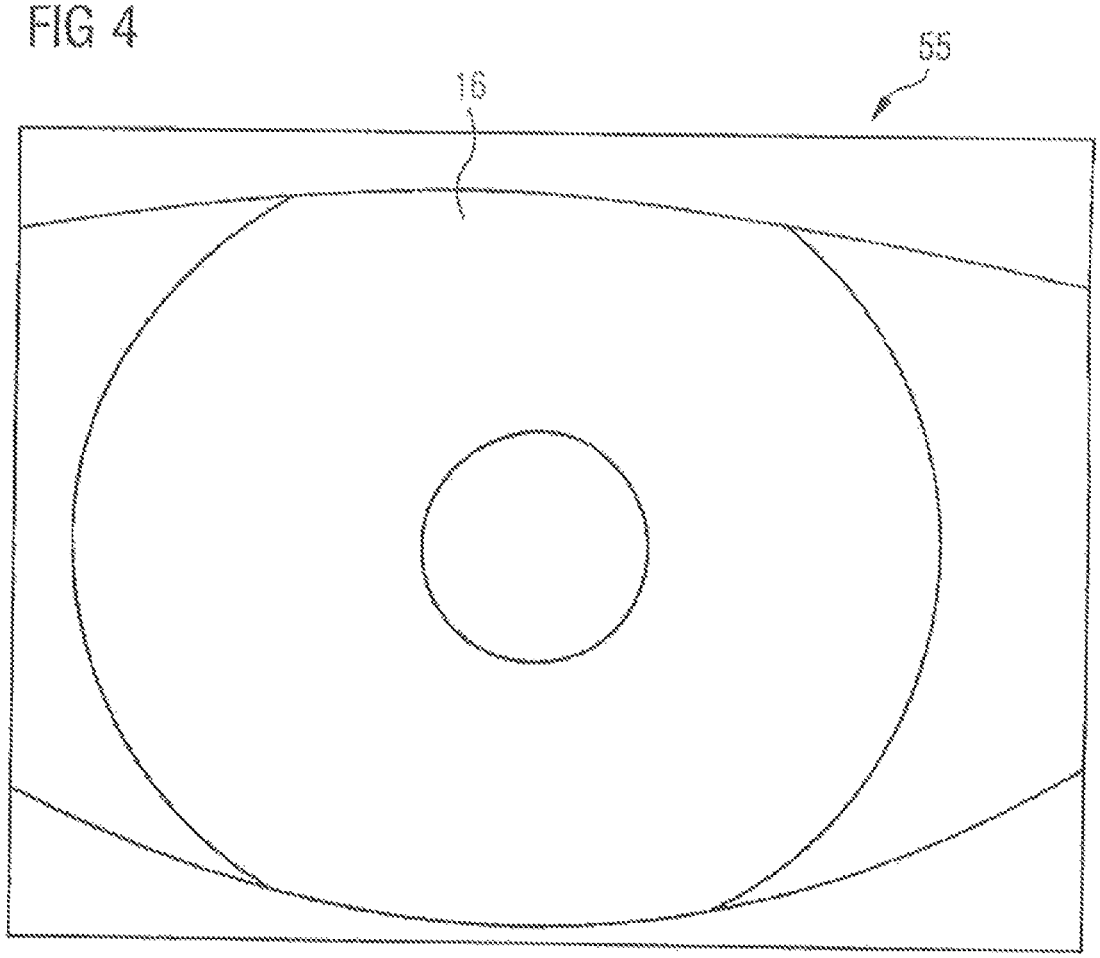
Figure 5:
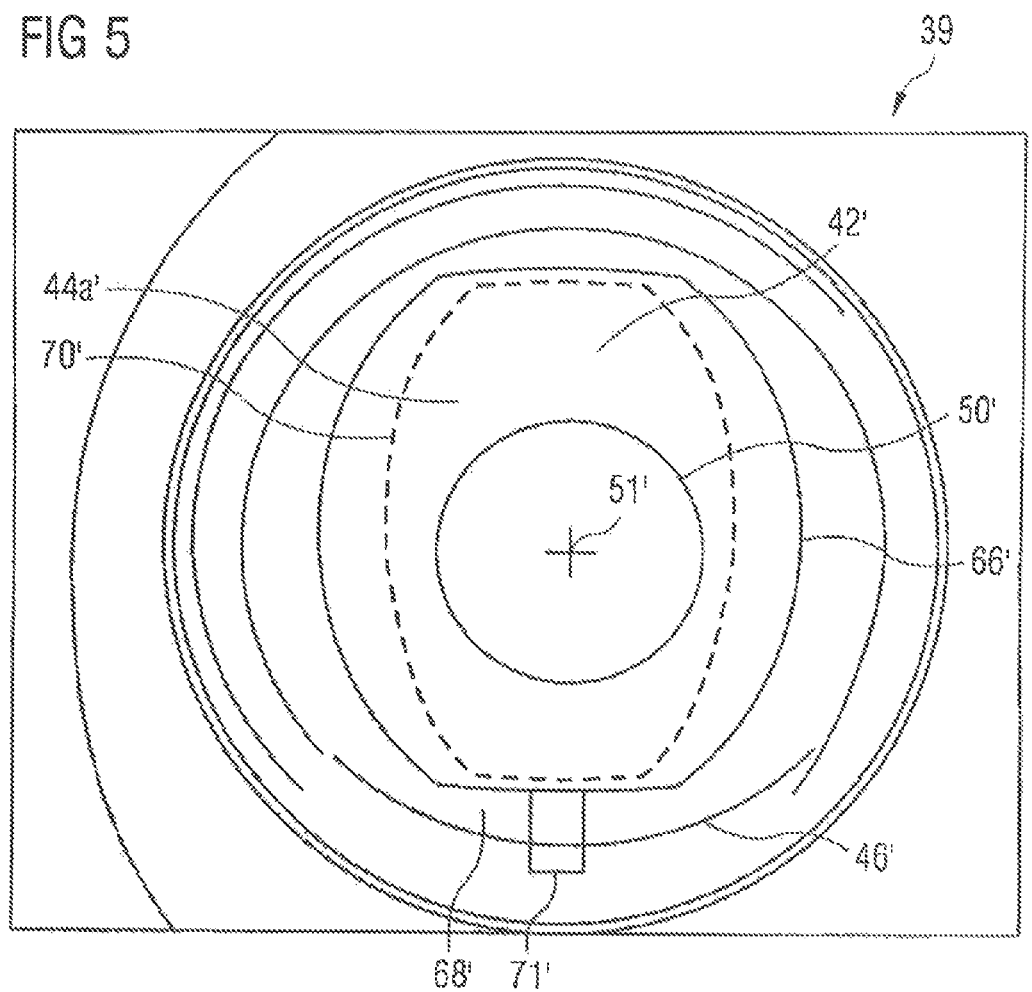
Figure 6:
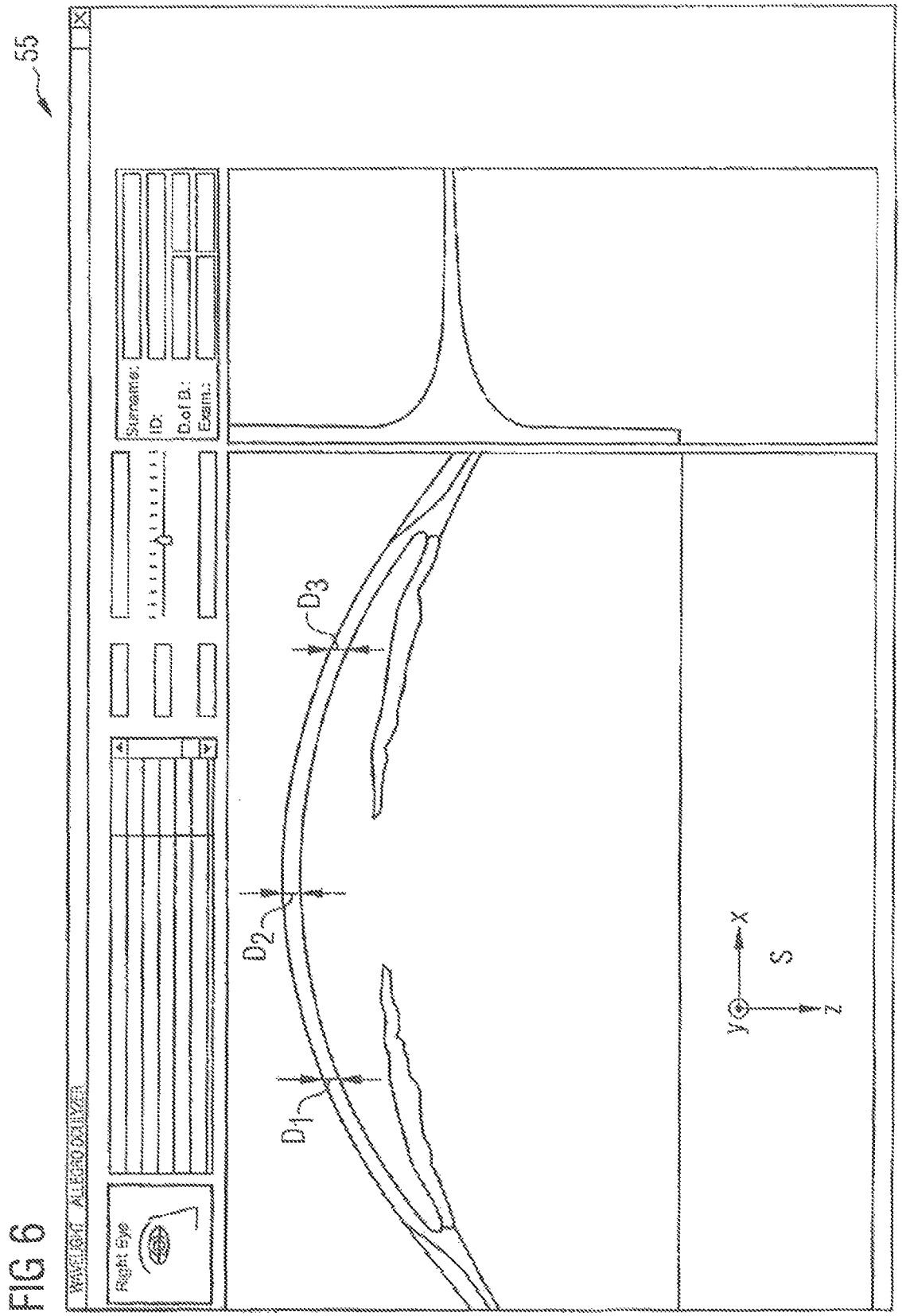
Figure 7:
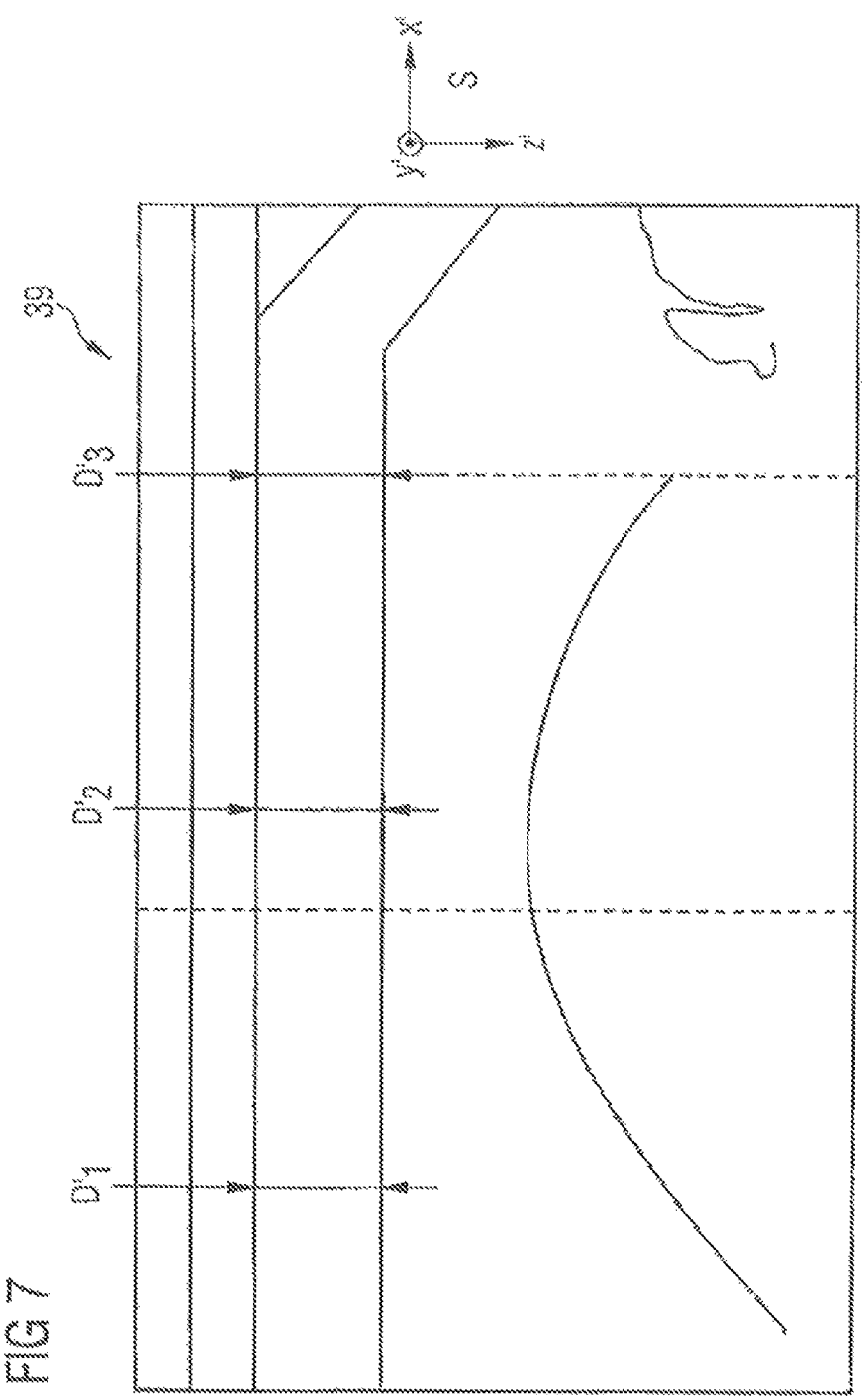
Figure 8:
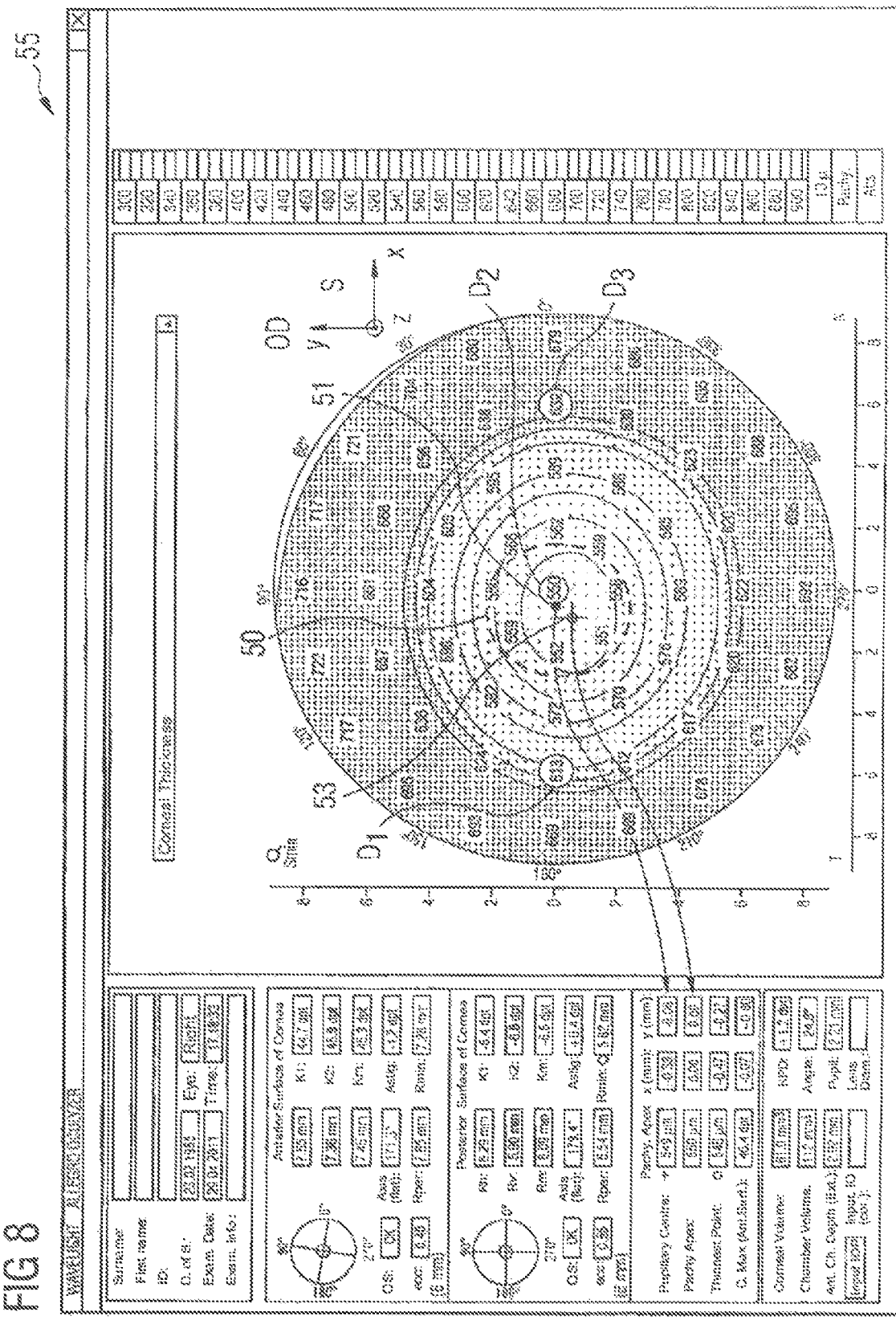

The invention will be elucidated further in the following on the basis of the accompanying drawings, in which:

FIG. 1 shows an overall representation of an apparatus for an eye-surgery treatment system according to an embodiment, FIG. 2a shows a schematic representation of an image generated by an image-acquisition unit of the apparatus represented in FIG. 1, into which several projected images generated by a computer arrangement of the apparatus have been inserted, FIG. 2b shows a schematic representation of a diagnostic image generated by a diagnostic instrument of the apparatus represented in FIG. 1, FIG. 3 shows an overall representation of a method for an eye-surgery treatment according to an embodiment, FIG. 4 shows a further representation of a diagnostic image generated by a diagnostic instrument of the apparatus represented in FIG. 1, FIG. 5 shows a further representation of an image generated by an image-acquisition unit of the apparatus represented in FIG. 1, into which several projected images generated by a computer arrangement of the apparatus have been inserted, FIG. 6 shows a representation of an incision profile, generated by a diagnostic instrument of the apparatus represented in FIG. 1 for generating a diagnostic image, FIG. 7 shows a representation of an incision profile, generated by an image-acquisition unit of the apparatus represented in FIG. 1 for generating an image, and FIG. 8 shows a further representation of a diagnostic image generated by a diagnostic instrument of the apparatus represented in FIG. 1.

In FIG. 1, components of a laser-assisted eye-surgery treatment system 10 have been represented schematically. This treatment system 10 includes a laser 12 which provides a laser beam 14 consisting of short-pulse laser radiation, for example with pulse durations within the attosecond, femtosecond or picosecond range. The laser beam 14 is directed, via means described in more detail below for beam control and beam shaping, onto a human eye 16 to be treated. The eye 16 is fixed with the aid an applicator 18 in an x',y',z' coordinate system S' of the treatment system 10. The applicator 18 includes a contact element 20, represented here in exemplary manner as a plane-parallel applanation plate that is transparent to the laser radiation and that, for example, is pressed against the eye 16 so that the eye 16 conforms to the contact element 20 with its anterior surface. The applicator 18 further includes a support body 21 for the contact element 20, the support body 21 having been represented here in exemplary manner as a conically widening sleeve body which in the region of its wider sleeve end is capable of being releasably coupled to a focusing objective which is not represented in any detail.

The laser beam 14 is directed via several mirrors 22, 24, 26 into the aforementioned focusing objective (for example, an f-theta objective). In the exemplary case shown, mirrors 22, 24 are capable of swivelling about mutually perpendicular tilting axes, so that by appropriate drive of mirrors 22, 24 the site of the focus of the laser beam 14 in the x',y' plane (i.e. transverse to the direction of beam propagation at the eye 16) can be adjusted. For the purpose of longitudinal local control of the site of the focus (i.e. in the z'-direction), for example a lens that is adjustable along the beam path of the laser beam 14, a lens with variable refractive power, or an adaptive optical mirror (ao mirror) may have been provided (not represented in any detail), with which the divergence of the laser beam 14 and hence the z'-position of the beam focus can be influenced. In the exemplary case shown, mirror 26 takes the form of an immovable dichroic deflecting mirror.

A program-controlled computer arrangement 28 with a data memory 30, with a scan-software module 32 for time-dependent local control of the radiation focus of the laser beam 14 in the coordinate system S' of the treatment system 10, and with an image-processing software module 34 serves as control unit of the treatment system 10.

A first image-acquisition unit 36 has been arranged behind the dichroic mirror 26. The image-acquisition unit 36 is, for example, a digital CCD camera, an OCT image-acquisition unit and/or a Scheimpflug image-acquisition unit with, in each instance, suitable imaging optics. A green-light source 38 which casts green light onto the eye 16 has been assigned to the image-acquisition unit 36. The image-acquisition unit 36 acquires a two-dimensional (x'-y' plane in coordinate system S'), digital and true-to-scale image 39 (cf. FIG. 2a and FIG. 5) of the eye 16. The image 39 shown in FIG. 2a and FIG. 5 is a top view of the eye 16. The image 39 includes at least one projected image of at least one first feature of the eye 16. In the image 39 in FIG. 2a, scleral blood vessels 40', 40a' of the sclera 41', the iris 42' with structural features 44a', 44b', the limbus 46' with a structural feature 48', and the pupillary margin 50' with a structural feature 52' have been shown by way of exemplary features. In the image 39 in FIG. 5, the iris 42' with a structural feature 44a', the limbus 46' and the pupillary margin 50' with the pupillary centre 51' have been shown by way of exemplary features. In the following it will be assumed in exemplary manner that scleral blood vessel 40' is being used as first feature.

The image-acquisition unit 36 supplies image data, which represent the image 39, to the computer arrangement 28. The image-processing software module 34 processes these image data and evaluates them in a manner yet to be elucidated.

Diagnostically determined reference data may be stored in advance in the memory 30. For the purpose of determining the reference data, in the exemplary case of FIG. 1 which is shown a diagnostic instrument 54 has been provided which includes a second image-acquisition unit 56, by means of which, in a preliminary examination of the eye 16 taking place temporally ahead of the laser treatment, a two-dimensional, digital and true-to-scale diagnostic image 55 (cf. FIG. 2b, FIG. 4 and FIG. 8) of the eye 16 to be treated can be acquired in an x,y,z coordinate system S of the diagnostic instrument. As can be discerned, for example, in FIG. 4 and FIG. 6, the eye 16 is not loaded or deformed by external action during the preliminary examination, so the internal pressure of the eye 16 has its natural value. The image-acquisition unit 56 includes, for example, a digital camera and also a topographer (ophthalmometer, keratometer or videokeratographer) configured to acquire a topography of the cornea of the eye 16 and therefrom to assign to each pixel of the diagnostic image 55 a curvature value that is representative of a surface curvature of the cornea at a lateral position of the cornea corresponding to the pixel. The data acquired by the camera and by the topographer enter jointly into the diagnostic image 55.

The diagnostic image 55 according to FIG. 2b, FIG. 4 and FIG. 8 is a z-top view of the eye 16. The diagnostic image 55 (FIG. 2b) also contains projected images of the same structures which are also to be seen in the image 39 (FIG. 2a). These structures are denoted in FIG. 2b by the same reference symbols as in FIG. 2a, but without added dash. Therefore the diagnostic image 55 according to FIG. 2b contains a projected image of the sclera 41, projected images of scleral blood vessels 40, 40a, a projected image of the iris 42 with structural features 44a, 44b, a projected image of the limbus 46 with a structural feature 48, and also a projected image of the pupillary margin 50 with a structural feature 52. For the purpose of better detection of the eye-internal features, the diagnostic instrument 54 exhibits a green-light source 58. Furthermore, the diagnostic instrument 54 includes an image-processing unit 60 which is able to detect two defined selected features of the eye 16 on the basis of the data supplied by the image-acquisition unit 56. In the present example, scleral blood vessel 40 serves as first feature. An astigmatically curved corneal region 64, which is characterised by two astigmatism axes 64a, 64b intersecting in FIG. 2b in the centre of the pupil, serves as second feature.

The image processing unit 60 is configured to detect the first feature 40 in the diagnostic image 55 by virtue of three characteristic points $R_1$, $R_2$, $R_3$ of the first feature 40 which do not lie on a common straight line. The three points $R_1$, $R_2$, $R_3$ represent in the present example the ends of three arteries of scleral blood vessel 40 extending from a central point. The positions of points $R_1$, $R_2$, $R_3$ are determined in the coordinate system S of the diagnostic instrument 54 and are uniquely defined by three corresponding vectors $R_1$, $R_2$, $R_3$ (vectors have been represented here in bold type).

The position of the first feature 40 has been uniquely defined in coordinate system S by the vectors $R_1$, $R_2$, $R_3$. Similarly, the orientation of the first feature 40 in coordinate system S has been uniquely defined by vectors $R_1$, $R_2$, $R_3$ or by two of the three relative vectors $R_2-R_1$, $R_3-R_1$, $R_3-R_2$. For example, these are the two vectors $r_{12}$ and $r_{13}$, where $$r_{12}=R_2-R_1$$

$$r_{13}=R_3-R_1.$$

The size and the shape of the first feature are also uniquely characterised by points $R_1$, $R_2$, $R_3$. Since points $R_1$, $R_2$, $R_3$ do not lie on a straight line, vectors $r_{12}$ and $r_{13}$ are linearly independent and span in the diagnostic image 55 an eye-internal coordinate system which is individual to the eye 16.

The image-processing unit 60 is furthermore configured to detect the second feature 64 in the diagnostic image 55 by virtue of three characteristic points $P_1$, $P_2$, $P_3$ equally not lying on a straight line, and to represent these three points $P_1$, $P_2$, $P_3$ by three corresponding vectors $P_1$, $P_2$, $P_3$ in the eye-internal coordinate system that is spanned by vectors $r_{12}$ and $r_{13}$. As can be discerned in FIG. 2b, points $P_1$ and $P_2$ lie in exemplary manner on one of the two astigmatism axes 64a, 64b. The diagnostic instrument can in this way determine the position, the orientation, the size and the shape of the second feature 64 on the basis of the determination of the coefficients $a_1$, $a_2$, $a_3$, $b_1$, $b_2$, $b_3$ in $$P_1=a_1 \times r_{12}+b_1 \times r_{13}$$

$$P_2=a_2 \times r_{12}+b_2 \times r_{13}$$

$$P_3=a_3 \times r_{12}+b_3 \times r_{13}.$$

The points $P_1$, $P_2$, $P_3$ of the second feature 64 are consequently referenced with respect to the coordinate system defined by the first feature 40, the origin of which is formed by point $R_1$. The coefficients $a_1$, $a_2$, $a_3$, $b_1$, $b_2$, $b_3$ are individual to the eye 16 and independent of the choice of the coordinate system S. The coefficients $a_1$, $a_2$, $a_3$, $b_1$, $b_2$, $b_3$ can be stored in a database 62 as reference data jointly with digital image data of the diagnostic image 55 and with information from which it is evident which is the first feature 40 with respect to which the second feature 64 has been referenced. In FIG. 1 the database 62 has been integrated into the diagnostic instrument 54. But the database may also have been formed independently of any instrument or external to any instrument, that is to say, for instance as an online database, as a mobile data carrier (diskette, CD, DVD, USB stick, memory card, . . . ), etc.

For the laser treatment of the eye 16, in the course of which an incision figure is to be produced in the eye 16 by laser technology by stringing photodisruptions together, the reference data are read out from the database 62 and communicated to the computer arrangement 28. The dividing line 65 drawn in dashed manner in FIG. 1 is intended to make it clear that the treatment station at which the laser 12, the computer arrangement 28 and the image-acquisition unit 36 are located may be spatially separated from the diagnostic station with the diagnostic instrument 54, and that the determination of the reference data takes place temporally ahead of the laser treatment of the eye 16.

The image-processing software module 34 of the computer arrangement 28 has access to the database 62, reads the reference data, stored therein, of the patient in question, and determines, on the basis of the reference data, what the first feature 40' is to be detected by. Subsequently the image-processing software module 34 determines, from the image 39 according to FIG. 2a acquired by the image-acquisition unit 36, the positions of the corresponding characteristic points $R_1'$, $R_2'$, $R_3'$ of the first feature 40' in coordinate system S' on the basis of coefficients $c_1$, $c_2$, $c_3$, $d_1$, $d_2$, $d_3$, whereby the following holds:

$$R_1'=c_1 \times x'+d_1 \times y'$$

$$R_2'=c_2 \times x'+d_2 \times y'$$

$$R_3'=c_3 \times x'+d_3 \times y'.$$

Coordinate system S' is spanned by three vectors x', y', z', where z' runs parallel to the direction of the laser beam 14 and consequently is not acquired in the two-dimensional image 39. From the coefficients $c_1$, $c_2$, $c_3$, $d_1$, $d_2$, $d_3$ the image-processing unit 34 now determines the representation of relative vectors $r_{12}'$, $r_{13}'$ according to $$r_{12}'=R_2'-R_1'$$

$r_{13}'=R_3'-R_1'$.

From this, the computer arrangement 28 can calculate the relative positions of points $P_1'$, $P_2'$, $P_3'$ in relation to points $R_1'$, $R_2'$, $R_3'$ by means of $P_1'=a_1 \times r_{12}'+b_1 \times r_{13}'+R_1'$ $P_2'=a_2 \times r_{12}'+b_2 \times r_{13}'+R_1'$ $P_3'=a_3 \times r_{12}'+b_3 \times r_{13}'+R_1'$, this being effected as a function of the coefficients $a_1$, $a_2$, $a_3$, $b_1$, $b_2$, $b_3$ previously determined by the diagnostic instrument 54 and included in the reference data.

The computer arrangement 28 can consequently determine the positions of the points $P_1'$, $P_2'$, $P_3'$ characterising the second feature 64', and hence the position and the orientation of the second feature 64' in the coordinate system S' of the treatment system 10, without thereby having to detect the second feature 64' itself directly in the image data acquired by the image-acquisition unit 36. Also, the size and the shape of the second feature 64' in coordinate system S' can be determined automatically, since the image 39 and the diagnostic image 55 are true-to-scale projected images of the eye 16, and on the basis of the size of the first feature 40, 40' in the image 39 or in the diagnostic image 55 a scaling (zooming) can be performed by the computer arrangement 28.

The computer arrangement 28 can also determine from the relative location of vectors $r_{12}$, $r_{13}$ in relation to $r_{12}'$, $r_{13}'$ an angle of rotation by which coordinate system S has been rotated in relation to coordinate system S' with respect to the z-axis or z'-axis. Any orientations of the eye 16 in the x'-y' plane (for instance, by virtue of rotations of the eye 16 about the z'-axis) can in this way be detected by the computer arrangement 28 and incorporated by the treatment system 10 into the determination of the position, orientation, size and shape of the incision figure, without this having to be performed manually by a physician or surgeon.

On the basis of the positions $P_1'$, $P_2'$, $P_3'$ and the orientations $P_1'$-$P_2'$, $P_3'$-$P_2'$, $P_2'$-$P_1'$ established therefrom, the size and shape of the second feature 64' in the coordinate system S' the scan software module 32 automatically calculates an incision FIG. 66' to be produced in the eye 16. In the exemplary case shown, the incision FIG. 66' defines a corneal flap with a hinge 68' (in the specialist terminology often designated, even in German, by the English term "hinge") represented by a hinge axis $Q_1'$-$Q_2'$. In addition, the incision FIG. 66' further includes an auxiliary incision 71'.

The auxiliary incision offers a degassing channel, through which surgical gases that arise in the course of the photodisruptive machining of the eye tissue can be vented. A penetration of such gases into critical tissue regions of the eye can be avoided in this way. It is preferred firstly to produce the auxiliary incision; only then is the flap cut.

After the flap has been cut, it is folded aside, connected to the hinge 68', in order to expose corneal tissue (stroma) which is then machined in an ablation zone 70', in accordance with a previously determined ablation profile, with an excimer laser, not represented in any detail, of the treatment system 10, in order to correct the weakness of vision of the eye 16 (that is to say, the astigmatism of the eye 16) caused by the second feature 64' (that is to say, the astigmatically curved corneal region). The incision FIG. 66' is adapted in its position, orientation, size and shape by the scan software module 32 to the position, orientation, size and shape of the second feature 64'. The positions of points $Q_1'$, $Q_2'$ are calculated by $Q_1'=u_1 \times P_1'+v_1 \times P_2'$ $Q_2'=u_2 \times P_1'+v_2 \times P_2'$ $Q_3'=u_3 \times P_1'+v_3 \times P_2'$ The coordinates $u_1$, $u_2$, $u_3$, $v_1$, $v_2$, $v_3$ are treatment-specific and have been adapted to the weakness of vision characterised by the second feature 64'. The coordinates $u_1$, $u_2$, $u_3$, $v_1$, $v_2$, $v_3$ are, for example, adapted in such a way that the hinge axis $Q_1'$-$Q_2'$ of the hinge has been oriented perpendicular to the astigmatism axis $P_1'$-$P_2'$, points $Q_1'$ and $Q_2'$ have the same spacing from the astigmatism axis $P_1'$-$P_2'$, and with respect to their lateral positions (that is to say, along x' and y' in coordinate system S') have been arranged in a region of the iris 42' approaching the limbus 46', see FIG. 2a.

The position, orientation, shape and/or size of the auxiliary incision 71' are treatment-specific and have been adapted to the position and orientation of the hinge 68', in particular to the position and orientation of the hinge axis $Q_1'$-$Q_2'$. The auxiliary incision 71' extends from the cornea of the eye 16 to the sclera 41' of the eye 16 and passes through the limbus 46'. The auxiliary incision 71' which is formed in planar manner, substantially as a flat channel, is connected to the remaining incision FIG. 66' and terminates on the surface of the eye 16. The auxiliary incision 71' therefore makes it possible that gases arising in the course of the cutting of the flap and of the remaining incision FIG. 66' are able to escape from the eye 16.

The computer arrangement 28 is configured to generate a pictorial representation of the incision FIG. 66' and of the second feature 64' and also, where appropriate, of the ablation zone 70' in accordance with the position and orientation and also size and shape in coordinate system S' that have been determined for these elements. The treatment system 10 may include a device 72 configured to superimpose this pictorial representation on the image 39 acquired by the image-acquisition unit 36 and to display the overall image that has arisen therefrom—as represented in FIG. 2a—on an output instrument 74 (e.g. a monitor) in a manner that is true to scale. An overall image of such a type has been represented in FIG. 5. Alternatively or additionally, the device 72 can insert the pictorial representation into the observation image of an operating microscope of the treatment system 10 (not shown in any detail).

The position, orientation and dimensioning of the incision image 66' determined by the computer arrangement 28 can in this way be observed and monitored by the treating physician or surgeon in relation to the first feature 40' of the eye 16.

The incision FIG. 66' serves as a suggestion determined by the computer arrangement 28, which can be modified. If the physician/surgeon is dissatisfied with the suggestion, he/she can modify the position, orientation and dimensioning of the incision FIG. 66', in order to make the treatment even more ideal. For this purpose the physician/surgeon can make use of an input device 76 of the treatment system 10, which permits him/her to communicate desired modifications of the position, orientation, size or/and shape of the incision FIG. 66' to the computer arrangement 28 by manual input. The computer arrangement 28 takes these modifications into account and re-determines the position, orientation, size or/and shape of the incision FIG. 66' appropriately. Since the displayed/inserted visualisation of the incision FIG. 66' always reflects the current position, orientation, size and shape of the incision FIG. 66' relative to the second feature 64' in the image 39, this optimisation can be effected by the physician/surgeon online, as it were.

As soon as the physician/surgeon is satisfied with the position, orientation, size and shape of the incision FIG. 66' or, to be more precise, with the visualised representation of the same, he can confirm the current incision FIG. 66' manually by input via the input device 76. Subsequently the treatment system 10 then produces the incision FIG. 66' confirmed by the physician/surgeon in the eye 16 of the patient by means of the laser 12.

In FIG. 3 the treatment procedure just described has been represented once again in the form of a flow chart. Firstly, in a preliminary examination S102 of the eye 16 taking place temporally ahead of the laser treatment S100, a recording of the iris representing the diagnostic image 55 (cf. FIG. 2*b* and FIG. 4) of the eye 16 to be treated is acquired, see step S104. From the recording of the iris, image data are generated which represent individual features 40-52 of the eye 16, see step S106. Within the scope of a feature extraction S108, position, orientation and size of the first feature 40 in the x,y,z coordinate system S of the diagnostic instrument 54 are determined. In addition, diagnostic data are determined in parallel, see step S110. The diagnostic data include, in particular, keratometer values, a corneal thickness distribution (as represented in FIG. 8) and also position, orientation and size (length) of the astigmatism axes 64*a*, 64*b* (as represented in FIG. 2*b*) in coordinate system S. The data determined during the preliminary examination S102 are stored in a database or on a data carrier, see step S112.

After the preliminary examination S102 has been concluded, the actual laser treatment S100 takes place. For this purpose, in step S114 the eye 16 to be treated is docked onto the applanation lens 20 of the treatment system 10, and in step 116 an image 39 of the eye 16 is recorded. Within the scope of a feature extraction S118, position, orientation and size of the first feature 40' in the x',y',z' coordinate system S' of the treatment system 10 are determined. By matching of the position, orientation and size, determined in this way, of the first feature 40' in coordinate system S' with the position, orientation and size, read out from the data memory or database, of the first feature 40 in coordinate system S, the position, orientation, and size (length) of the astigmatism axes 64*a*', 64*b*' in coordinate system S' are determined by computation.

In step S122, on the basis of the previously determined diagnostic data, in particular the keratometer values, parameters for an ablation profile are calculated which have been adapted to the position, orientation and size (length) of the astigmatism axes 64*a*', 64*b*' in coordinate system S'. In order also actually to be able to expose this ablation profile in the eye 16 for the purpose of machining, in step S124 the position, the orientation, the shape and the size of the incision FIG. 66', including the corresponding positions, orientations, shapes and sizes of the flap, of the hinge and of the auxiliary incision 71' are calculated. In step S126 the incision FIG. 66' calculated in this way is, together with the recording acquired in step S116, displayed on a graphical user interface (GUI) or/and inserted by a suitable insertion device (in the manner of a head-up display, HUD) into the observation beam path of the operating microscope (see also FIG. 2*b* and FIG. 5).

Position, orientation, shape and size of the incision FIG. 66' can be modified by an operating surgeon conducting the treatment, see step S130. In the course of a modification S132 the operating surgeon changes the parameters proposed by the treatment system by manual setting via the GUI. After this, the incision FIG. 66' is re-determined in accordance with the modification and re-displayed on the GUI or in the HUD. As soon as the operating surgeon is satisfied with the position, orientation, shape and size of the incision FIG. 66', he/she confirms the set parameters in step S134. After this, the treatment of the eye 16 is undertaken by the treatment system 10 in accordance with the set parameters, see step S136. Alternatively it is also conceivable that the second feature represents a pathological tissue region of the eye 16 of a patient, which is clouding the sight of the patient, such as, for example, a cataract region, that is to say, a region that has become diseased with so-called grey cataract. The incision FIG. 66' then has to be determined in its position, orientation, size and shape with respect to the cataract region, and has to be brought about in the human lens of the eye 16.

The diagnostic instrument 54 includes, for example, a digital camera and also a topographer (ophthalmometer, keratometer or videokeratographer) and is configured to acquire a topography of the cornea of the eye 16 and/or a corneal thickness distribution of the eye 16 and from this to assign to each pixel of the diagnostic image 55 a curvature value that is representative of a surface curvature of the cornea at a lateral position of the cornea corresponding to the pixel.

The diagnostic instrument 54 may furthermore be configured, within the scope of a pachymetric recording of the eye 16, to acquire a corneal thickness distribution of the eye 16, see FIG. 8. In this case, to each pixel of the diagnostic image 55 a thickness value is assigned that is representative of the thickness of the cornea at a lateral position of the cornea corresponding to the pixel. In this representation the pupillary margin 50, the pupillary centre 51 and the corneal apex 53 can be detected. The various thickness values, or, to be more precise, the corneal thickness distribution resulting from the thickness values, permit an individual characterisation of the eye. The corneal thickness distribution can therefore serve as the first feature. The corneal thickness distribution then defines an eye-internal coordinate system, with respect to which the position, orientation and size of the second feature, for instance an astigmatically deformed corneal region or astigmatism axes, are referenced. For this purpose, for example, the corneal apex 53 can be chosen as origin of coordinates (x [mm]=0, y=[mm]).

The corneal thickness distribution is determined, for example, on the basis of an OCT measurement or a Scheimpflug measurement. In the case of an OCT measurement a plurality of two-dimensional incision profiles of the eye 16 are acquired, on the basis of which two-dimensional and/or three-dimensional projected images of the eye 16 are possible. For example, for this purpose the incision profiles run parallel to one another or intersect one another along an axis of the eye (visual axis, optical axis of the eye, . . . ). An incision profile of such a type can be seen in FIG. 6. The diagnostic instrument 54 determines from the incision profiles in each instance the thickness values of the cornea along the cross section corresponding to the respective incision profile. In exemplary manner, three thickness values $D_1$, $D_2$, $D_3$ of the cornea have been labelled in FIG. 6. The totality of the thickness values yield in their spatial assignment the corneal thickness distribution as represented in FIG. 8. Regions of constant thickness appear as contour lines. For the purpose of better differentiation of the various contour lines, the same have been colour-coded. From an OCT image, characteristic layer distributions can also be extracted.

Just like the diagnostic instrument 54, the treatment system 10 may be configured, within the scope of a pachymetric recording of the eye 16, to acquire the corneal thickness distribution of the eye 16. In FIG. 7 an OCT recording has been represented which shows an incision profile of the cornea in the course of the treatment and from which thickness values for the corneal thickness distribution are obtained. The cornea in this case is in a flattened state which is brought about with the aid of the applanation lens 20. In exemplary manner, in FIG. 7 three thickness values $D_1'$, $D_2'$, $D_3'$ of the cornea corresponding to the thickness values $D_1$, $D_2$, $D_3$ shown in FIG. 6 have been labelled.

Since the corneal thickness distribution remains unchanged both in the applanated state and in the relaxed state, the referencing, determined during the preliminary examination with the aid of the diagnostic instrument 54, of the astigmatically deformed corneal region or of the astigmatism axes retains its validity during the actual treatment.

The invention claimed is:

1. Apparatus for a laser-assisted eye-surgery treatment system, comprising:
a first image-acquisition unit configured to acquire a first image of an eye to be treated; and
a computer arrangement configured to:
detect, by image processing of the first image, at least one first feature of the eye;
determine a position and an orientation of the first feature in a coordinate system of the treatment system; and
determine a position and an orientation of an incision figure defining a corneal flap with a flap hinge to be produced in the eye in the treatment coordinate system of the treatment system, a beam path of the treatment system defining a z-axis of the treatment coordinate system, a plane normal to the beam path defining an xy-plane of the treatment coordinate system, the flap hinge defining a hinge axis in the xy-plane, the position and the orientation of the incision figure determined by:
defining a first feature coordinate system from coordinates of the first feature in a diagnostic image, wherein the z-axis of the first feature coordinate system is normal to the top view of the eye;
expressing a position and orientation of at least one second feature in the diagnostic image in the first feature coordinate system, the at least one second feature comprising an astigmatically curved corneal region, the location of the astigmatically curved corneal region described by an astigmatism axis in the xy-plane of the first feature coordinate system;
determining the position and orientation of the second feature in the first feature coordinate system according to the expression of the position and orientation of the second feature in the first feature coordinate system;
determining the position and orientation of the second feature in the treatment coordinate system from the position and orientation of the second feature in the first feature coordinate system; and
determining the incision based on the position and orientation of the second feature in the treatment coordinate system and the astigmatism axis, the position and orientation of the flap hinge based on the astigmatism axis and defined by a predetermined set location condition between the hinge axis and the astigmatism axis.

2. Apparatus according to claim 1, wherein the set location specifies that the hinge axis and the astigmatism axis are substantially mutually perpendicular.

3. Apparatus according to claim 1, wherein the at least one first feature has been assigned to an iris, a pupil, a limbus, a scleral blood-vessel arrangement or a corneal thickness distribution of the eye.

4. Apparatus according to claim 1, including a diagnostic instrument with a second image-acquisition unit for acquiring a second image of the eye to be treated, the diagnostic instrument being configured to detect in the second image, by image processing, the at least one first feature, and to generate feature information relating to a position and orientation of each of the two features.

5. Apparatus according to claim 4, wherein the computer arrangement is configured to determine, on the basis of the feature information, the relative position and orientation of the second feature in relation to the first feature.

6. Apparatus according to claim 4, wherein the diagnostic instrument and the first image-acquisition unit have been assigned to various workstations in a medical practice.

7. Apparatus according to claim 4, wherein a database has been assigned to the diagnostic instrument, in order to store therein the feature information or information derived therefrom, with assignment to patient-identifying information, and wherein the computer arrangement has access to the database.

8. Apparatus according to claim 1, wherein the computer arrangement is configured to bring about a pictorial representation of the incision figure that illustrates the determined position and orientation of the incision figure in relation to the first feature or to the second feature or to a corneal region to be ablated.

9. Apparatus according to claim 8, wherein the computer arrangement is configured to bring about the pictorial representation on a monitor or by insertion into an observation beam path of an operating microscope.

10. Apparatus according to claim 8, wherein the computer arrangement is configured to modify the determined position or orientation of the incision figure in accordance with a user input and to modify the pictorial representation of the incision figure in accordance with the modified position or orientation.

11. Apparatus according to claim 1, wherein the computer arrangement is configured to receive a confirmation, entered by the user, for the position and orientation of the incision figure and to generate, in a manner depending on the reception of this confirmation, control data for a laser device and to control the laser device in accordance with these control data for the purpose of producing the incision figure in the eye.

12. Apparatus according to one of claims 2 to 11, wherein the incision figure further defines an auxiliary channel that extends from an incision surface of the flap in the direction away from the flap, the computer arrangement being configured to produce, in a manner depending on the determined position and orientation of at least those parts of the incision figure which define the flap, control data for the production of the auxiliary channel in such a manner that the auxiliary channel extends at least into the region of the limbus of the eye.

13. Apparatus according to claim 12, wherein the computer arrangement is configured to generate the control data for the production of the auxiliary channel in such a manner that the auxiliary channel extends beyond the limbus of the eye.

* * * * *